US012592315B2

(12) United States Patent
Colombo et al.

(10) Patent No.: US 12,592,315 B2
(45) Date of Patent: *Mar. 31, 2026

(54) APPARATUS, SYSTEM, METHOD, AND COMPUTER-READABLE RECORDING MEDIUM FOR DISPLAYING TRANSPORT INDICATORS ON A PHYSIOLOGICAL MONITORING DEVICE

(71) Applicant: Drägerwerk AG & Co. KGaA, Lübeck (DE)

(72) Inventors: Lianna Colombo, Phoenix, AZ (US); Philip Collins, Nashua, NH (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 15 days.

This patent is subject to a terminal disclaimer.

(21) Appl. No.: 18/678,982

(22) Filed: May 30, 2024

(65) Prior Publication Data

US 2024/0312612 A1      Sep. 19, 2024

Related U.S. Application Data

(63) Continuation of application No. 18/073,680, filed on Dec. 2, 2022, now Pat. No. 12,020,810, which is a
(Continued)

(51) Int. Cl.
*G16H 40/20*      (2018.01)
*A61B 5/00*       (2006.01)

(52) U.S. Cl.
CPC ............. *G16H 40/20* (2018.01); *A61B 5/002* (2013.01); *A61B 5/0024* (2013.01); *A61B 5/7435* (2013.01)

(58) Field of Classification Search
CPC ...... G16H 40/20; A61B 5/002; A61B 5/0024; A61B 5/7435
(Continued)

(56) References Cited

U.S. PATENT DOCUMENTS

| | | | | |
|---|---|---|---|---|
| 5,936,539 A | * | 8/1999 | Fuchs | G16H 40/67 |
| | | | | 455/100 |
| 10,679,746 B1 | * | 6/2020 | Fletcher | G16H 40/20 |

(Continued)

FOREIGN PATENT DOCUMENTS

| | | | | |
|---|---|---|---|---|
| WO | WO-2013095459 A1 | * | 6/2013 | G16H 10/65 |

*Primary Examiner* — Alaaeldin M. Elshaer
(74) *Attorney, Agent, or Firm* — Nolte Lackenbach Siegel

(57) ABSTRACT

A physiological monitoring device includes: a sensor interface, a display configured to display information related to the patient, and at least one processor. The at least one processor is configured to: operate the physiological monitoring device into a non-transport mode while docked to one of at least one monitor mount; display first location context information corresponding to a first patient care area on the display while the physiological monitoring device is operating in the non-transport mode in the first patient care area; detect an undocking event in response to undocking the physiological monitoring device from a first monitor mount of the at least one monitor mount, wherein the first monitor mount is located in the first patient care area; and in response to detecting the undocking event, operate the physiological monitoring device in a transport mode, including changing the first location context information to transport context information on the display.

17 Claims, 9 Drawing Sheets

Related U.S. Application Data continuation of application No. 16/882,457, filed on May 23, 2020, now Pat. No. 11,545,259.

(60) Provisional application No. 62/852,470, filed on May 24, 2019.

(58) Field of Classification Search
USPC ........................................................ 705/2, 3
See application file for complete search history.

(56) References Cited

U.S. PATENT DOCUMENTS

| | | | |
|---|---|---|---|
| 11,348,681 B1* | 5/2022 | Morrow | G16H 10/60 |
| 2011/0047298 A1* | 2/2011 | Eaton | G06F 1/1632 |
| | | | 710/304 |
| 2013/0073302 A1* | 3/2013 | Ryan | G16H 40/20 |
| | | | 705/2 |
| 2013/0109928 A1* | 5/2013 | Menzel | G06F 3/0601 |
| | | | 600/301 |
| 2015/0302539 A1* | 10/2015 | Mazar | G08B 21/02 |
| | | | 705/3 |
| 2021/0196121 A1* | 7/2021 | Aarnio | A61B 5/002 |
| 2022/0040035 A1* | 2/2022 | Higgins | A61B 5/7445 |

* cited by examiner

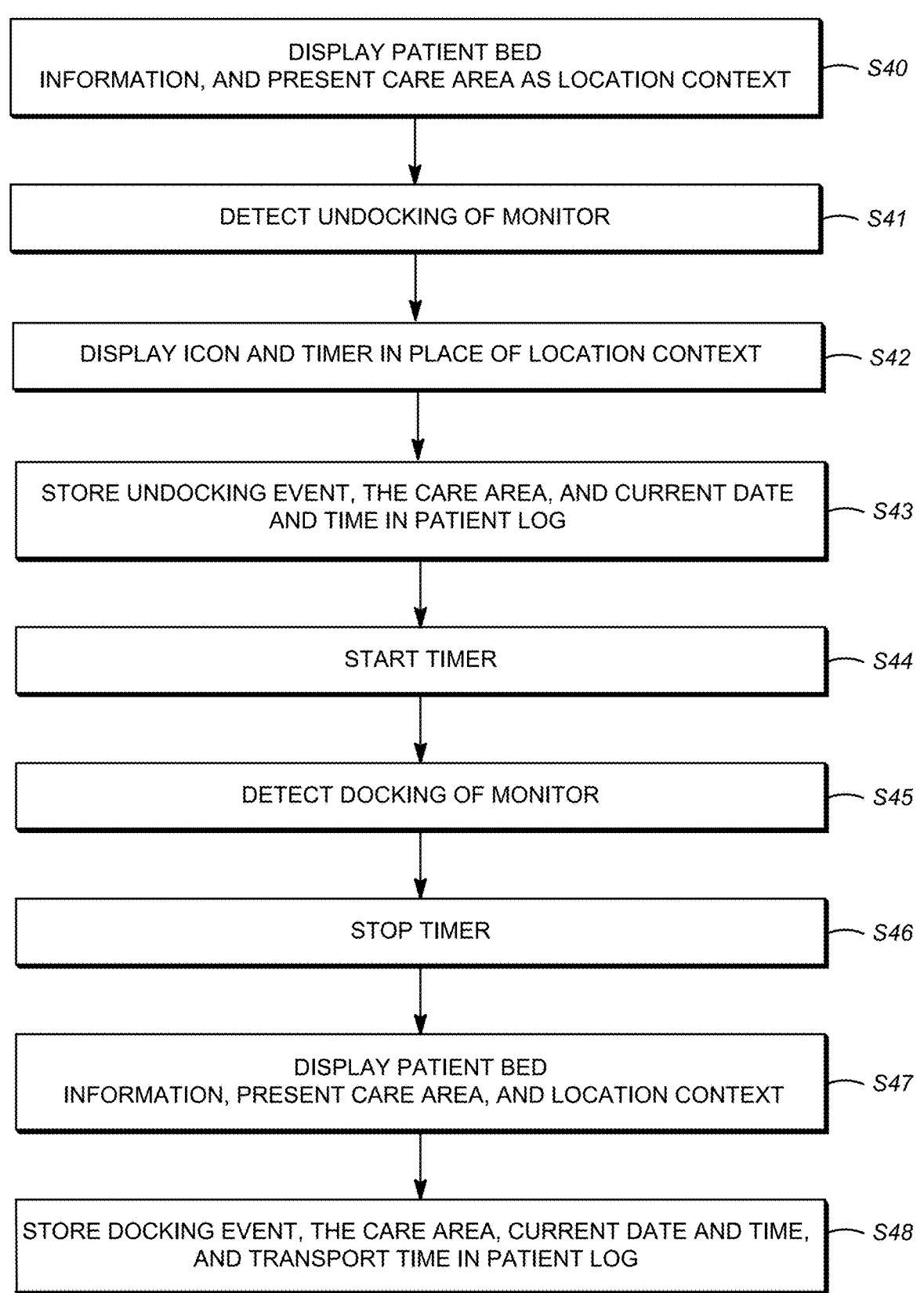

DISPLAY PATIENT BED
INFORMATION, AND PRESENT CARE AREA AS LOCATION CONTEXT    ~ S40

DETECT UNDOCKING OF MONITOR    ~ S41

DISPLAY ICON AND TIMER IN PLACE OF LOCATION CONTEXT    ~ S42

STORE UNDOCKING EVENT, THE CARE AREA, AND CURRENT DATE
AND TIME IN PATIENT LOG    ~ S43

START TIMER    ~ S44

DETECT DOCKING OF MONITOR    ~ S45

STOP TIMER    ~ S46

DISPLAY PATIENT BED
INFORMATION, PRESENT CARE AREA, AND LOCATION CONTEXT    ~ S47

STORE DOCKING EVENT, THE CARE AREA, CURRENT DATE AND TIME,
AND TRANSPORT TIME IN PATIENT LOG    ~ S48

*FIG. 4*

| DATE | TIME | DURATION | PRIO. | ALARM MESSAGE | VALUE |
|---|---|---|---|---|---|
| 03-SEP-2018 | 17:30:31 | 9 SEC | ⊠ | AFib | 38 bpm |
| 03-SEP-2018 | 17:28:46 | 9:42 MIN | | DOCKED: OR3 | |
| 03-SEP-2018 | 17:26:56 | 5 SEC | !! | HR LOW | 32 bpm |
| 03-SEP-2018 | 17:24:45 | 53 SEC | ! | ART OUT OF RANGE LOW | ••mmHg |
| 03-SEP-2018 | 17:23:02 | 15 SEC | !! | RRi HIGH | 32 /min |
| 03-SEP-2018 | 17:19:12 | 1:01 HR | ! | SPO₂ CHECK SENSOR | |
| 03-SEP-2018 | 17:19:04 | | | UNDOCKED: ICU5 | |

DETECT UNDOCKING OF MONITOR ⌐ S80

START TIMER ⌐ S81

RECEIVE LOCATION INFORMATION OF MONITOR ⌐ S82

CROSS-REFERENCE LOCATION INFORMATION TO HOSPITAL LAYOUT ⌐ S83

DETERMINE TRANSPORT ACTIVITY AND ESTIMATED ARRIVAL TIME OF PATIENT ⌐ S84

STORE TRANSPORT ACTIVITY AND TRANSMIT ESTIMATED ARRIVAL TIME ⌐ S85

APPARATUS, SYSTEM, METHOD, AND COMPUTER-READABLE RECORDING MEDIUM FOR DISPLAYING TRANSPORT INDICATORS ON A PHYSIOLOGICAL MONITORING DEVICE

CROSS-REFERENCE TO RELATED APPLICATIONS

This application is a continuation of application Ser. No. 18/073,680, filed on Dec. 2, 2022, which is a continuation of application Ser. No. 16/882,457 filed on May 23, 2020, which claimed the benefit of U.S. Prov. Pat. App. Ser. No. 62/852,470,filed on May 24, 2019. Priority to and the benefit of U.S. Prov. Pat. App. Ser. No. 62/852,470, Ser. No. 16/882,457, and Ser. No. 18/073,680 are hereby claimed for all purposes, including the right of priority.

FIELD

The subject matter of the present disclosure relates generally to the use of indicators for representing the transport of a patient in a patient care environment.

BACKGROUND

Clinicians often administer medicines prior to transporting a patient between care areas within a hospital or between different hospitals or patient care facilities. Therefore, it can be critical to a patient's care to know the status of the patient during transport as well as an estimated time of arrival.

Currently, there is no efficient and useful way to utilize transport information on a physiological monitoring device that reduces cognitive load on clinicians during transport, and supports rapid patient assessment and accurate clinical documentation. Useful transport information can reduce stress on clinicians in emergency situations and provide information for establishing hospital transport efficiency analytics.

Transport indicators refer to both the elapsed time of a specific patient transfer and the transport location of the patient when being transferred between care areas. Transport indicators would allow clinicians to have a quick reference for the duration of a transport to help manage medicines, and patient comfort and care. Transport start and stop times, along with the transport duration, can subsequently be used to assist with event analysis and documentation.

Additionally, transport location information can support hospital emergency code situations in which a crisis team is required to intervene by communicating the patient's location and offering an estimated time to arrival (ETA) for assistance. The transport location information can support an ETA to another care area, and provide underlying data to support the optimization of transport paths and care area scheduling.

Thus, it would be advantageous and an improvement over the relevant technology to provide an apparatus, system, method, and computer-readable medium for quickly and efficiently displaying transport indicators on a physiological monitoring device in a way that reduces cognitive load on clinicians during transport of patients, and supports rapid patient assessment and more accurate clinical documentation.

SUMMARY

One or more embodiments provide a method for displaying transport indicators related to a patient transport on a physiological monitoring device. The method includes: operating the physiological monitoring device in a non-transport mode while docked to one of at least one monitor mount; displaying first location context information corresponding to a first patient care area on a display of the physiological monitoring device while the physiological monitoring device is in the non-transport mode in the first patient care area; the physiological monitoring device detecting an undocking event in response to undocking the physiological monitoring device from a first monitor mount of the at least one monitor mount, wherein the first monitor mount is located in the first patient care area; and in response to detecting the undocking event, the physiological monitoring device switching into a transport mode, including changing the first location context information to transport context information on the display.

One or more embodiments provide a non-transitory computer-readable medium having computer-readable instructions stored thereon which when executed by a physiological monitoring device cause the physiological monitoring device to perform a method. The method includes: operating the physiological monitoring device in a non-transport mode while docked to one of at least one monitor mount; displaying first location context information corresponding to a first patient care area on a display of the physiological monitoring device while the physiological monitoring device is in the non-transport mode in the first patient care area; detecting an undocking event in response to undocking the physiological monitoring device from a first monitor mount of the at least one monitor mount, wherein the first monitor mount is located in the first patient care area; and in response to detecting the undocking event, operating the physiological monitoring device into a transport mode, including changing the first location context information to transport context information on the display.

One or more embodiments provide a physiological monitoring device, including: a sensor interface configured to receive physiological data from at least one physiological sensor connected to a patient; a display configured to display information related to the patient; and at least one processor. The at least one processor is configured to: operate the physiological monitoring device into a non-transport mode while docked to one of at least one monitor mount; display first location context information corresponding to a first patient care area on the display while the physiological monitoring device is operating in the non-transport mode in the first patient care area; detect an undocking event in response to undocking the physiological monitoring device from a first monitor mount of the at least one monitor mount, wherein the first monitor mount is located in the first patient care area; and in response to detecting the undocking event, operate the physiological monitoring device in a transport mode, including changing the first location context information to transport context information on the display.

BRIEF DESCRIPTION OF THE DRAWINGS

In the drawings, like reference numbers generally indicate identical, functionally similar, and/or structurally similar elements.

FIG. 4 illustrates a method for displaying transport indicators related to a patient on a physiological monitoring device according to one or more embodiments of the present disclosure;

FIG. 7B illustrates a segment of a patient transport log according to one or more embodiments of the present disclosure;

DETAILED DESCRIPTION

Figure 1:
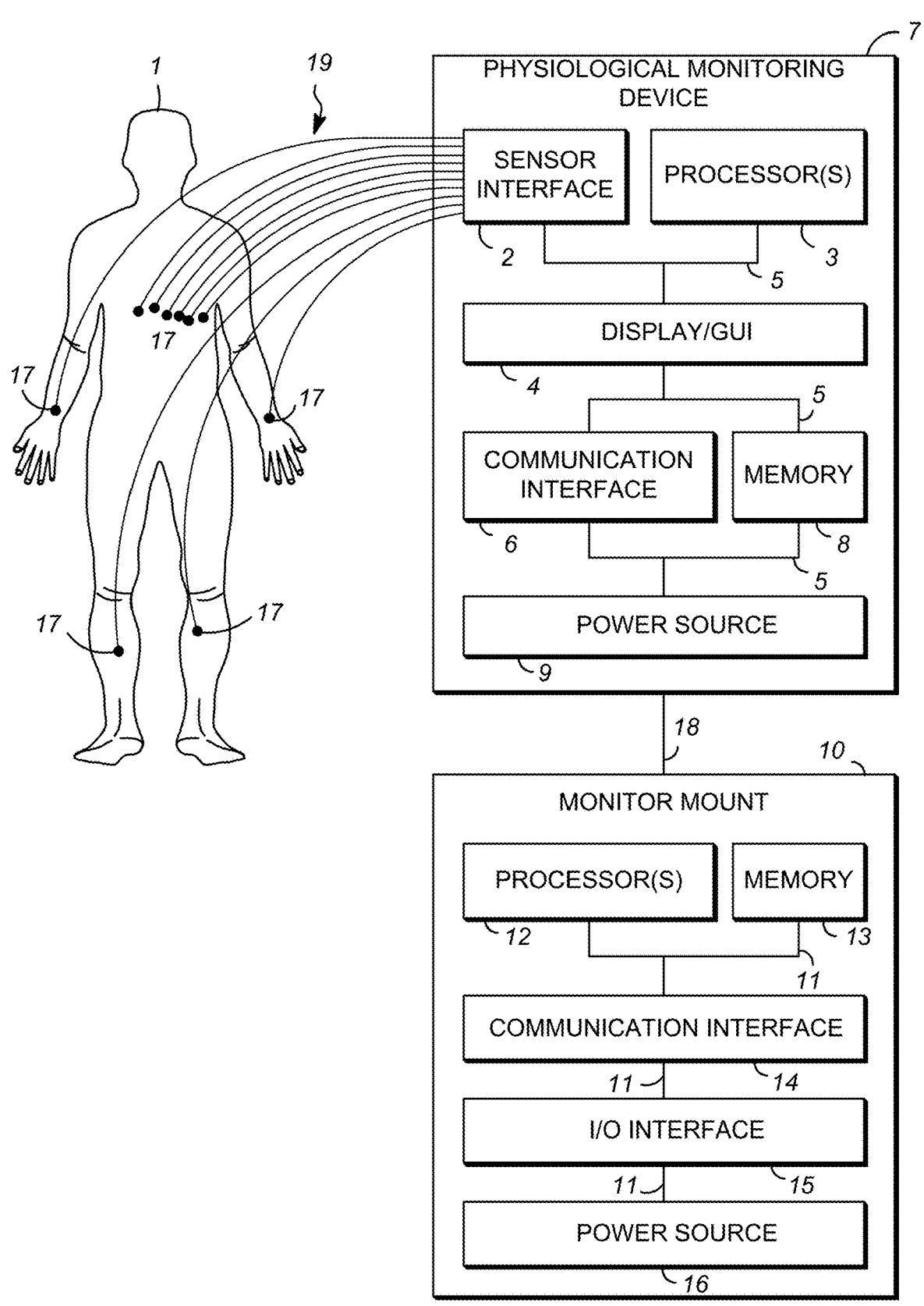
FIG. 1 is a schematic diagram of a system for displaying transport indicators related to a patient on a physiological monitoring device.

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

FIG. 1 is a schematic diagram of a system for displaying transport indicators related to a patient on a physiological monitoring device. As shown in FIG. 1, the system includes a physiological monitoring device 7 capable of receiving physiological data from various sensors 17 connected to a patient 1, and a monitor mount 10 to which the physiological monitoring device 7 is removably mounted or docked.

In general, it is contemplated by the present disclosure that the physiological monitoring device 7 and the monitor mount 10 include electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the physiological monitoring device 7 and the monitor mount 10 may be adapted to execute any operating system, including Linux, UNIX, Windows Server, etc., as well as virtual machines adapted to virtualize execution of a particular operating system, including customized and proprietary operating systems. The physiological monitoring device 7 and the monitor mount 10 are further equipped with components to facilitate communication with other computing devices over one or more network connections, which may include connections to local and wide area networks, wireless and wired networks, public and private networks, and any other communication network enabling communication in the system.

As shown in FIG. 1, the physiological monitoring device 7 is, for example, a patient monitor implemented to monitor various physiological parameters of the patient 1 via the sensors 17. The physiological monitoring device 7 includes a sensor interface 2, one or more processors 3, a display/GUI 4, a communications interface 6, a memory 8, and a power source 9. The sensor interface 2 can be implemented in hardware or combination of hardware and software and is used to connect via wired and/or wireless connections 19 to one or more sensors 17 for gathering physiological data from the patient 1. The sensors 17 may be physiological sensors and/or medical devices configured to measure one or more of the physiological parameters and output the measurements via a corresponding one or more connections 19 to the sensor interface 2. Thus, the connections 19 represent one or more wired or wireless communication channels configured to at least transmit sensor data from a corresponding sensor 17 to the sensor interface 2.

By way of example, sensors 17 may include electrodes that attach to the patient for reading electrical signals generated by or passed through the patient 1. Sensors 17 may be configured to measure vital signs, measure electrical stimulation, measure brain electrical activity such as in the case of a electroencephalogram (EEG), measure blood oxygen saturation fraction from absorption of light at different wavelengths as it passes through a finger, measure a CO2 level and/or other gas levels in an exhalation stream using infrared spectroscopy, measure oxygen saturation on the surface of the brain or other regions, measure cardiac output from invasive blood pressure and temperature measurements, measure induced electrical potentials over the cortex of the brain, measure blood oxygen saturation from an optical sensor coupled by fiber to the tip of a catheter, and/or measure blood characteristics using absorption of light.

The data signals from the sensors 17 include, for example, sensor data related to an electrocardiogram (ECG), non-invasive peripheral oxygen saturation (SpO2), non-invasive blood pressure (NIBP), body temperature, tidal carbon dioxide (etCO2), apnea detection, and/or other physiological data, including those described herein. The one or more processors 3 are used for controlling the general operations of the physiological monitoring device 7, as well as processing sensor data received by the sensor interface 2. Each one of the one or more processors 3 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the physiological monitoring device 7.

The display/GUI 4 is configured to display various patient data, sensor data, and hospital or patient care information, and includes a user interface implemented for allowing interaction and communication between a user and the physiological monitoring device 7. The display/GUI 4 includes, but is not limited to, a keyboard, a liquid crystal display (LCD), cathode ray tube (CRT) display, thin film transistor (TFT) display, light-emitting diode (LED) display, high definition (HD) display, or other similar display device that may include touch screen capabilities. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators). The use of transport indicators will be described in more detail with reference to FIGS. 4-6.

The communications interface 6 enables the physiological monitoring device 7 to directly or indirectly (via, for example, the monitor mount 10) communicate with one or more computing networks and devices, including one or more sensors 17, workstations, consoles, computers, monitoring equipment, alert systems, and/or mobile devices (e.g., a mobile phone, tablet, or other hand-held display device). The communications interface 6 can include various network cards, interfaces, communication channels, cloud, antennas, and/or circuitry to enable wired and wireless communications with such computing networks and devices. The communications interface 6 can be used to implement, for example, a Bluetooth connection, a cellular network connection, and/or a Wi-Fi connection with such computing networks and devices. Example wireless communication connections implemented using the communications interface 6 include wireless connections that operate in accordance with, but are not limited to, IEEE802.11 protocol, a Radio Frequency For Consumer Electronics (RF4CE) protocol, and/or IEEE802.15.4 protocol (e.g., Zig-Bee protocol). In essence, any wireless communication protocol may be used.

Additionally, the communications interface 6 can enable direct (i.e., device-to-device) communications (e.g., messaging, signal exchange, etc.) such as from the monitor mount 10 to the physiological monitoring device 7 using, for example, a universal serial bus (USB) connection or other communication protocol interface. The communications interface 6 can also enable direct device-to-device connection to other device such as to a tablet, computer, or similar electronic device; or to an external storage device or memory.

The memory 8 can be a single memory device or one or more memory devices at one or more memory locations that include, but is not limited to, a random access memory (RAM), a memory buffer, a hard drive, a database, an erasable programmable read only memory (EPROM), an electrically erasable programmable read only memory (EEPROM), a read only memory (ROM), a flash memory, hard disk, various layers of memory hierarchy, or any other non-transitory computer readable medium. The memory 8 can be used to store any type of instructions and patient data associated with algorithms, processes, or operations for controlling the general functions and operations of the physiological monitoring device 7.

The power source 9 can include a self-contained power source such as a battery pack and/or include an interface to be powered through an electrical outlet (either directly or by way of the monitor mount 10). The power source 9 can also be a rechargeable battery that can be detached allowing for replacement. In the case of a rechargeable battery, a small built-in back-up battery (or super capacitor) can be provided for continuous power to be provided to the physiological monitoring device 7 during battery replacement. Communication between the components of the physiological monitoring device 7 (e.g., components 2, 3, 4, 6, 8, and 9) are established using an internal bus 5.

As shown in FIG. 1, the physiological monitoring device 7 is connected to the monitor mount 10 via a connection 18 that establishes a communication connection between, for example, the respective communications interfaces 6, 14 of the devices 7, 10. The connection 18 is an interface that enables the monitor mount 10 to detachably secure the physiological monitoring device 7 to the monitor mount 10. In this regard, "detachably secure" means that the monitor mount 10 can receive and secure the physiological monitoring device 7, but the physiological monitoring device 7 can also be removed or undocked from the monitor mount 10 by a user when desired. In other words, the physiological monitoring device 7 can be removably docked or removably mounted to the monitor mount 10 and the connection 18 forms an electrical connection between the devices 7, 10 for enabling communication therebetween. The connection 18 may also enable the transmission of power from the monitor mount 10 to the physiological monitoring device 7 for charging the power source 9. The connection 18 may also enable the physiological monitoring device 7 to detect whether it is in a docked or undocked state. Thus, the connection 18 may further enable the physiological monitoring device 7 via the interface to detect an undocking event and a docking event by detecting an electrical connection or an optical link, or an absence thereof, between the physiological monitoring device 7 and the monitor mount 10.

When the physiological monitoring device 7 is docked to the monitor mount 10, it can be regarded as being in a non-transport mode and may be configured to display a GUI or one or more GUI icons on display/GUI 4 specific to the non-transport mode. In contrast, when the physiological monitoring device 7 is undocked from the monitor mount 10, it can be regarded as being in a transport mode and may be configured to display a GUI or one or more GUI icons on display/GUI 4 specific to the transport mode. The connection 18 may include, but is not limited to, a USB connection, a parallel connection, a serial connection, a coaxial connection, a High-Definition Multimedia Interface (HDMI) connection, an optical connection, and/or any other electrical connection configured to connect electronic devices and transmit data and/or power therebetween.

The monitor mount 10 includes one or more processors 12, a memory 13, a communications interface 14, an I/O interface 15, and a power source 16. The one or more processors 12 are used for controlling the general operations of the monitor mount 10 and may be further used to controller one or more operations of the physiological monitoring device 7 when mounted to the monitor mount 10. Each one of the one or more processors 12 can be, but are not limited to, a CPU, a hardware microprocessor, a multi-core processor, a single core processor, an FPGA, a microcontroller, an ASIC, a DSP, or other similar processing device capable of executing any type of instructions, algorithms, or software for controlling the operation and performing the functions of the monitor mount 10.

The memory 13 can be a single memory or one or more memories or memory locations that include, but are not limited to a RAM, a memory buffer, a hard drive, a database, an EPROM, an EEPROM, a ROM, a flash memory, hard disk, or various layers of memory hierarchy, or any other non-transitory computer readable medium. The memory 13 can be used to store any type of instructions associated with algorithms, processes, or operations for controlling the general functions and operations of the monitor mount 10.

The communications interface 14 allows the monitor mount 10 to communicate with one or more computing networks and devices (e.g., the physiological monitoring device 7, workstations, consoles, computers, monitoring equipment, alert systems, and/or mobile devices (e.g., a mobile phone, tablet, or other hand-held display device). The communications interface 14 can include various network cards, interfaces, communication channels, antennas, and/or circuitry to enable wired and wireless communications with such computing networks and devices. The communications interface 14 can also be used to implement, for example, a Bluetooth connection, a cellular network connection, cloud-based connection, and a Wi-Fi connection. Example wireless communication connections implemented using the communications interface 14 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol). In essence, any wireless communication protocol may be used.

The communications interface 14 can also enable direct (i.e., device-to-device) communications (e.g., messaging, signal exchange, etc.) such as from the monitor mount 10 to the physiological monitoring device 7 using, for example, the connection 18. The communications interface 14 can enable direct (i.e., device-to-device) to other device such as to a tablet, PC, or similar electronic device; or to an external storage device or memory.

The I/O interface 15 can be an interface for enabling the transfer of information between monitor mount 10, one or more physiological monitoring devices 7, and external devices such as peripherals connected to the monitor mount 10 that need special communication links for interfacing with the one or more processors 12. The I/O interface 15 can be implemented to accommodate various connections to the monitor mount 10 that include, but is not limited to, a USB connection, a parallel connection, a serial connection, a coaxial connection, an HDMI connection, or any other electrical connection configured to connect electronic devices and transmit data therebetween.

The power source 16 can include a self-contained power source such as a battery pack and/or include an interface to be powered through an electrical outlet (either directly or by way of the physiological monitoring device 7). The power source 16 can also be a rechargeable battery that can be detached allowing for replacement. Communication between the components of the monitor mount 10 (e.g., components 12, 13, 14, 15 and 16) are established using an internal bus 11.

Figure 2:
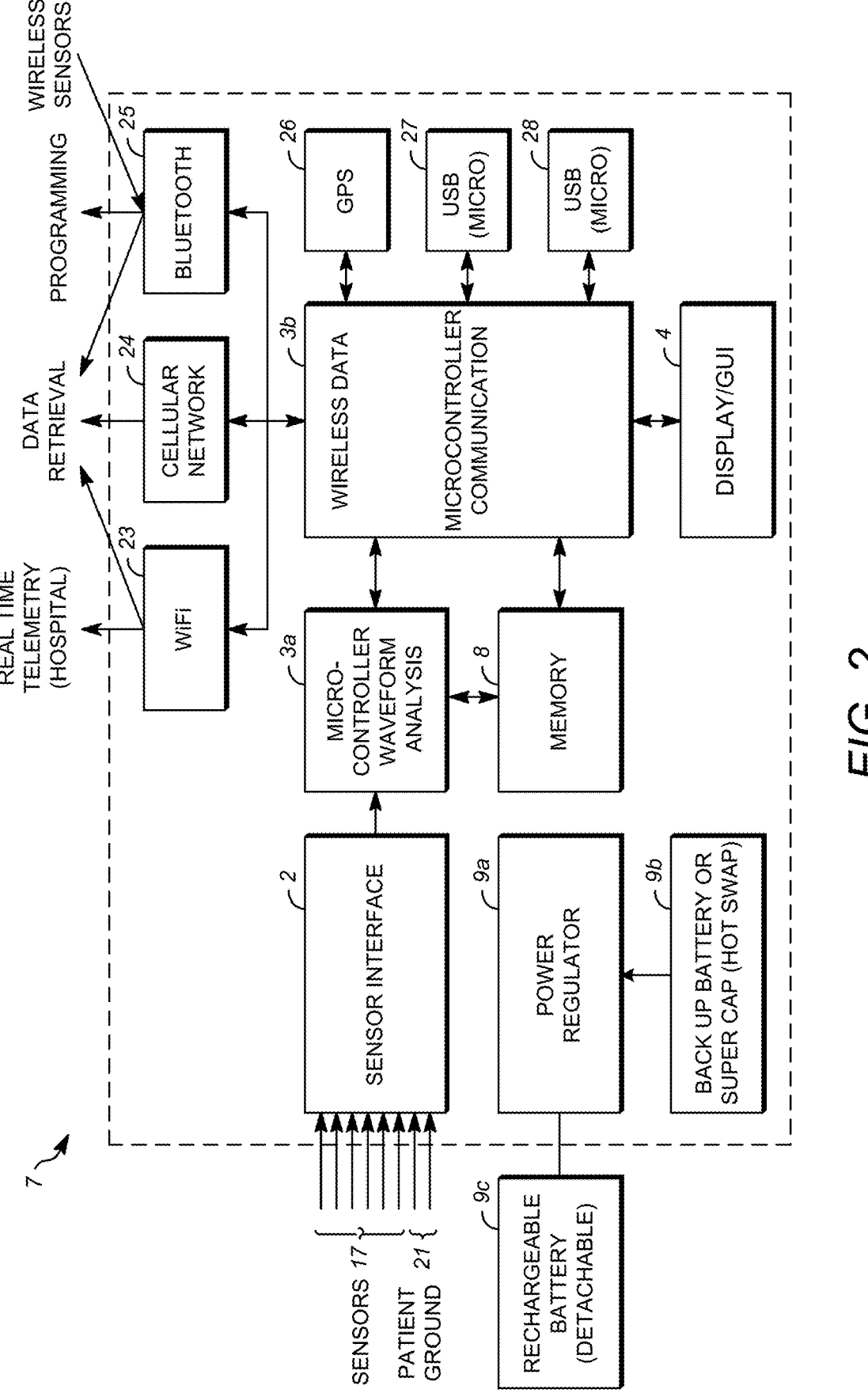
FIG. 2 is a schematic diagram of an exemplary physiological monitoring device according to one or more embodiments of the present disclosure.

FIG. 2 is a more detailed schematic diagram of the physiological monitoring device of FIG. 1 according to one or more embodiments of the present disclosure.

As shown in FIG. 2, the physiological monitoring device 7 is attached to one or more of several different types of sensors 17 configured to measure and readout physiological data related to the patient 1 (e.g., as shown on the left side of FIG. 1). One or more sensors 17 may be attached to physiological monitoring device 7 by, for example, a wired connection coupled to the sensor interface 2. Additionally, or alternatively, one or more sensors 17 may be a wireless sensor that is communicatively coupled to the physiological monitoring device 7 via the communication interface 6, which includes circuitry for receiving data from and sending data to one or more devices using, for example, a Wi-Fi connection 23, a cellular network connection 24, and/or a Bluetooth connection 25. The communications interface 6 shown in FIG. 1 is represented in FIG. 2 by the combination of microcontroller 3b and elements 23-28.

The data signals from the sensors 17 received by the physiological monitoring device 7 may include sensor data related to, for example, body temperature (BT), pulse (heart rate (HR)), and breathing rate (respiratory rate) (RR), an ECG, SpO2, NIBP, and/or etCO2.

The data signals received from the sensors, including an ECG sensor and an SpO2 sensor, can be analog signals. For example, the data signals for the ECG and the SpO2 are input to the sensor interface 2, which can include an ECG data acquisition circuit and an SpO2 data acquisition circuit. Both the ECG data acquisition circuit and the SpO2 data acquisition circuit may include amplifying and filtering circuitry as well as analog-to-digital (A/D) circuitry that converts the analog signal to a digital signal using amplification, filtering, and A/D conversion methods. In the event that the ECG sensor and the SpO2 sensor are wireless sensors, the sensor interface 2 may receive the data signals from the microcontroller 3b. Alternatively, the microcontroller 3b may have the appropriate data acquisition circuitry integrated therein and may itself be regarded as a sensor interface. Thus, a sensor interface is a component configured to interface with one or more sensors 17 and receive sensor data therefrom.

As another example, the data signals related to NIBP, body temperature, and etCO2 can be received from sensors 17 to the sensor interface 2, which can include a physiological parameter interface such as serial interface circuitry for receiving and processing the data signals related to NIBP, temperature, and etCO2. In FIG. 1, the ECG data acquisition circuit, an SpO2 data acquisition circuit, and physiological parameter interface are described as part of the sensor interface 2. However, it is contemplated by the present disclosure that the ECG data acquisition circuit, the SpO2 data acquisition circuit, and physiological parameter interface can be implemented as circuits separate from the sensor interface 2. In the event that the NIBP sensor, the temperature sensor, and the etCO2 sensor are wireless sensors, the sensor interface 2 may receive the data signals from the microcontroller 3b. Alternatively, the microcontroller 3b may have the appropriate data acquisition circuitry integrated therein.

The processing performed by the ECG data acquisition circuit, the SpO2 data acquisition circuit, and external physiological parameter interface may generate analog data waveforms or digital data waveforms that are analyzed by the microcontroller 3a. The processors 3 shown in FIG. 1 are represented in FIG. 2 as microcontrollers 3a and 3b. The microcontroller 3a, for example, analyzes the digital waveforms to identify certain digital waveform characteristics and threshold levels indicative of conditions (abnormal and normal) of the patient 1 using one or more monitoring methods. A monitoring method may include comparing an analog or a digital waveform characteristic or an analog or digital value to one or more threshold values and generating a comparison result based thereon. The microcontroller 3a is, for example, a processor, an FPGA, an ASIC, a DSP, a microcontroller, or similar processing device. The microcontroller 3a includes a memory or uses a separate memory 8. The memory is, for example, a RAM, a memory buffer, a hard drive, a database, an EPROM, an EEPROM, a ROM, a flash memory, a hard disk, or any other non-transitory computer readable medium.

The memory stores software or algorithms with executable instructions and the microcontroller 3a can execute a set of instructions of the software or algorithms in association with executing different operations and functions of the physiological monitoring device 7 such as analyzing the digital data waveforms related to the data signals from the sensors 17. The results of the operations performed by the microcontroller 3a are passed to the microcontroller 3b.

Similar to microcontroller 3a, the microcontroller 3b is, for example, a processor, an FPGA), an ASIC, a DSP, a microcontroller, or similar processing device. The microcontroller 3b includes a memory or uses the separate memory 8. The memory is, for example, a RAM, a memory buffer, a hard drive, a database, an EPROM, an EEPROM, a ROM, a flash memory, a hard disk, or any other non-transitory computer readable medium. In some embodiments the microcontroller 3a is integrated with the microcontroller 3b as a single microcontroller or may share at least one processor and/or at least one memory.

As noted above, in FIG. 2, the communication interface 6 shown in FIG. 1 is represented by the combination of microcontroller 3b and elements 23-28. For example, the microcontroller 3b includes communication interface circuitry for establishing communication connections with various devices and networks using both wired and wireless connections, and transmitting physiological data, patient information, and transport information (e.g., transport times and patient location information), analysis results (e.g., comparison results) of the analysis performed by the microcontroller 3a, and alerts and/or alarms generated automatically in response to the analysis results to the patient 1, clinicians, and/or caregivers.

Patient information and transport information may be combined to generate additional transport information that tracks a status and/or condition of the patient 1. The status and/or condition of the patient may be an actual (measured) status or condition, or an expected status or condition that is based on, for example, an initial status or an initial condition of a patient at the initiation of a transport and a lapsed transport time.

By way of example, the additional transport information may correspond to a medication and/or dosage amount administered prior to or during transport monitored in combination with an elapsed transport time, and may be used to track a re-administering of the medication or treatment during transport. For example, if an elapsed transport time has exceeded a threshold duration corresponding to a next scheduled administration of a medicine or treatment, the microcontroller 3b may trigger an event as well as an alarm. The microcontroller 3b may generate event data and enter the event data into a patient log, or more specifically a patient transport log corresponding to the patient. The microcontroller 3b may reference a patient's patient care schedule to determine a time corresponding to a patient's next scheduled administration of a medicine or treatment, and trigger the event/alarm when that scheduled time as been surpassed.

The memory 8 stores software or algorithms with executable instructions and the microcontroller 3b can execute a set of instructions of the software or algorithms in association with establishing the communication connections.

As shown in FIG. 2, wireless communication connections established by the communication interface circuitry of microcontroller 3b include a Bluetooth connection 25, a cellular network connection 24, and a Wi-Fi connection 23. The wireless communication connections can allow, for example, patient and hospital information, alerts, and physiological data to be transmitted in real-time within a hospital wireless communications network (e.g., Wi-Fi) as well as allow for patient and hospital information, alerts, and physiological data to be transmitted in real-time to other devices (e.g., Bluetooth 25 and/or cellular networks 24).

It is also contemplated by the disclosure of the present application that the communication connections established by the microcontroller 3b enable communications over other types of wireless networks using alternate hospital wireless communications such as wireless medical telemetry service (WMTS), which can operate at specified frequencies (e.g., 1.4 GHz). Other wireless communication connections can include wireless connections that operate in accordance with, but are not limited to, an IEEE802.11 protocol, a RF4CE protocol, and/or an IEEE802.15.4 protocol (e.g., ZigBee protocol).

The Bluetooth connection 25 can also be used to provide the transfer of data to a nearby device (e.g., a tablet) for review of data and/or changing of operational settings of physiological monitoring device 7. The microcontroller 3b of the physiological monitoring device 7 provides a communication connection by direct wired (e.g., hard-wired) connections as well for transferring data using, for example, a USB connection 27 to a tablet, a computer, or similar electronic device; or using, for example, a USB connection 28 to an external storage device or memory.

Additionally, the microcontroller 3b includes a connection to a display or graphical user interface (GUI) 4 for displaying patient information, transport information (e.g., transport times and patient location information), physiological data or measured data, and/or alerts/alarms to the patient, clinicians, and/or caregivers proximate to the physiological monitoring device 7 or within the wireless network. Although the physiological monitoring device 7 is described in FIG. 1 as having two microcontrollers 3a and 3b, it is contemplated by the disclosure of the present application that one microcontroller can be implemented to perform the functions of the two microcontrollers 3a and 3b.

The display/GUI 4 is, for example, an LCD display, a CRT display, a TFT display, an LED display, an HD display, or other similar display device that may include touch screen capabilities. The display/GUI 4 also provides a means for inputting instructions or information directly to the physiological monitoring device 7.

As shown in FIG. 2, whether the physiological monitoring device 7 is docked in a monitor mount 10 or separated therefrom, the physiological monitoring device 7 is maintained in proximity with the patient 1. The physiological monitoring device 7 includes a global positioning system (GPS) or other location data system 26 that can be connected to the communication interface circuitry of microcontroller 3b so that the physiological monitoring device 7 can transmit to the clinician, caregiver, or other devices the location of the patient 1 corresponding to the location of the physiological monitoring device 7 continuously and/or at predetermined intervals. The location of the patient 1 may be transmitted at all times including during transport. Additionally, the current location of the patient 1 can be used by the microcontroller 3b to determine an estimated time of arrival of the patient 1 at, for example, a predetermined destination. The microcontroller 3b may also use transport information, including location information acquired at different sample times (e.g., including a current sample time and one or more previous sample times) to determine whether the patient 1 is stationary or in motion.

The location data system 26 is configured determine a location of the physiological monitoring device 7 and generate location information based on determined the location. For example, location data provided by the location data system 26, which may include information pertaining to a floor level, a hallway or corridor, a terminal, a room number, or other location information used to determine a precise location within a building, can be compared to or cross-referenced to stored information related to a patient care facility layout (e.g., a hospital layout) or a patient care facility map (e.g., a hospital map) by the microcontroller 3b. The location data system 26 may also include an accelerometer or other motion detector device to detect movement of the physiological monitoring device 7.

The location data can be displayed on the display/GUI 4, as well as transmitted by the communication interface circuitry of microcontroller 3b to, for example, any of the aforementioned devices connected to the patient care facility wireless communications system.

In addition, the microcontroller 3b may compare or cross-reference the location data to information related to a patient care schedule (e.g., a treatment or a procedure scheduled for the patient 1 in a patient care area within the patient care facility) which further corresponds to a location within the patient care facility. For example, a location of the patient care area may define an end point (i.e., either a starting point or a terminus point) of a patient transport. Based on the comparison results, the microcontroller 3b can determine the estimated time of arrival of the patient 1 to or from the patient care area within the patient care facility. The estimated time of arrival can be displayed on the display/DUI 4, as well as transmitted by the communication interface circuitry of microcontroller 3b to, for example, any of the aforementioned devices connected to the patient care facility wireless communications system.

Additionally, the microcontroller 3b may be configured to determine whether the physiological monitoring device 7 is located within bounds of a predetermined area or a predetermined route. The predetermined area may correspond to one or more floor levels, one or more hallways or corridors, one or more terminals, one or more room numbers, or other location or section within a patient care facility. The predetermined area may be set or updated by an authorized person prior to, at the start of, or during transport of the patient 1. The predetermined area may be regarded as an authorized area in which the patient 1 is authorized to be in, delimited by one or more facility attributes. The predetermined area may be regarded as an authorized area in which the patient 1 has freedom of movement. The microcontroller 3b may determine whether the physiological monitoring device 7 is or is not located in the predetermined area. The microcontroller 3b may detect that the physiological monitoring device 7 has crossed a boundary defining the predetermined area.

The predetermined area may correspond the patient care facility as a whole, allowing the most freedom of movement within the facility. For example, the microcontroller 3b may determine that the physiological monitoring device 7 is no longer within the patient care facility when it becomes disconnected from the patient care facility wireless communications system or when it detects that the physiological monitoring device 7 has crossed an exit point of the patient care facility.

The predetermined area may define a boundary that, when the physiological monitoring device 7 moves outside of the predetermined area, for example, by crossing the boundary, the microcontroller 3b generates and transmits an alert over one or more wireless communication systems to a location monitoring device in order to notify personnel. The alert may include location information indicating a current location or a last detected location of the physiological monitoring device 7.

A predetermined route may be defined by two predetermined endpoints. The two predetermined endpoints may be entered before patient transport or updated during patient transport by authorized personnel. The predetermined route may be generated by the microcontroller 3b according to a patient care facility layout or a patient care facility map, automatically or through input from a user. The microcontroller 3b may monitor a transport of a patient along the predetermined route using sampled location information received from the location data system 26. The microcontroller 3b may trigger an alert over one or more wireless communication systems to a location monitoring device in order to notify personnel. The alert may include location information indicating a current location or a last detected location of the physiological monitoring device 7.

In addition, if it is determined by the microcontroller 3b that the physiological monitoring device 7 is not within or connected to the patient care facility wireless communications system (e.g., based on input from the location data system 26 or based on connectivity to the patient care facility wireless communications system), the microcontroller 3b may record and store pertinent physiological data in the memory 8. Additionally, if the Bluetooth connection 25 or WI-FI connection 23 are not available (e.g., out of transmission range or not operable), then the microcontroller 3*b* can store the physiological data in the memory 8 for later transmission when the Bluetooth connection or Wi-Fi connection becomes available.

The power source 9 shown in FIG. 1 is represented by elements 9*a*-9*c* in FIG. 2. As shown in FIG. 2, the power can be supplied using a rechargeable battery 9*c* that can be detached allowing for replacement. The rechargeable battery 9*c* is, for example, a rechargeable lithium-ion battery. Additionally, a small built-in back-up battery 9*b* (or super capacitor) is provided for continuous power to the physiological monitoring device 7 during battery replacement. A power regulator or regulation circuit 9*a* is provided between the rechargeable battery 9*c* and small back-up battery 9*b* to control which of batteries provide power to the physiological monitoring device 7. The physiological monitoring device 7 also includes a patient ground connection 21. The patient ground connection 21 can be used as a ground for single ended unipolar input amplifiers (e.g., precordial leads), or as a ground for bipolar input amplifiers (e.g., limb leads). It is also contemplated by the disclosure of the present application that the power regulator 9*a* can include a self-contained power source such as a battery pack and/or include an interface to be powered through an electrical outlet (either directly or by way of the monitor mount 10). Communication between the components of the physiological monitoring device 7 can be established using an internal bus similar to the internal bus 5 discussed with reference to FIG. 1.

Figure 3:
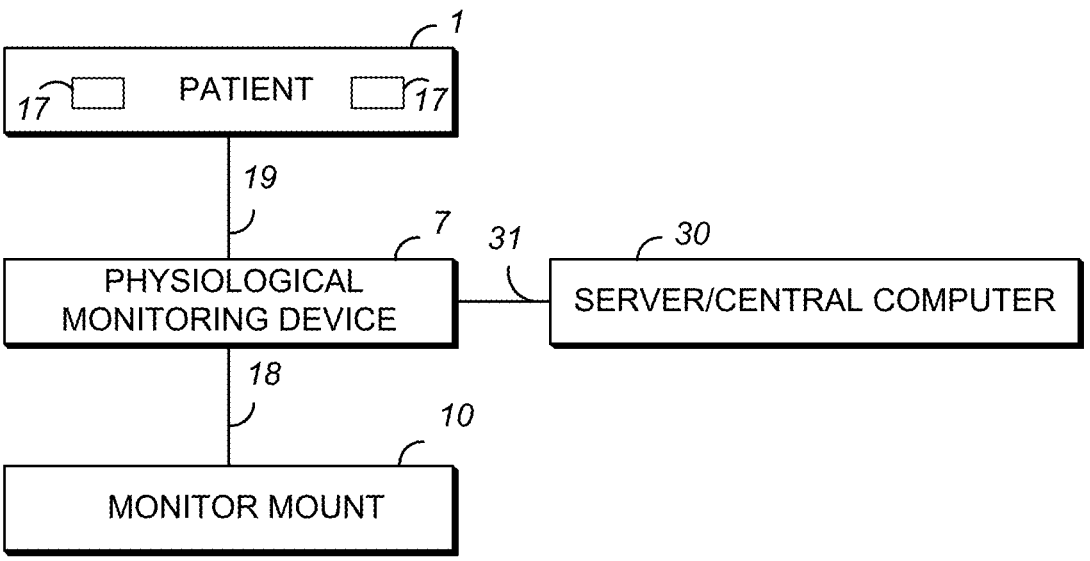
FIG. 3 is a schematic diagram of an exemplary system according to one or more embodiments of the present disclosure.

FIG. 3 is a schematic diagram of an exemplary system according to one or more embodiments of the present disclosure. FIG. 3 includes the patient 1, the physiological monitoring device 7, and the monitor mount 10 already discussed with reference to FIGS. 1 and 2. However, FIG. 3 also includes the addition of a server or central computer 30. As shown in FIG. 3, the physiological monitoring device 7 receives physiological data from various sensors 17 connected to the patient 1, and the physiological monitoring device 7 is removably mounted or docked to the monitor mount 10. The physiological monitoring device 7 is connected to the monitor mount 10 via a connection 18 that establishes a communication connection between, for example, the respective communications interfaces 6, 14 of the devices 7, 10. The connection 18 enables the monitor mount 10 to detachably secure the physiological monitoring device 7 to the monitor mount 10.

The physiological monitoring device 7 can also be connected to a server/central computer 30 via a wired or wireless connection 31 using the communication interface circuitry of the communications interface 6 of the physiological monitoring device 7 described with reference to FIGS. 1 and 2. The physiological monitoring device 7 can use the connection 31 as a communication channel to store patient and transport information (e.g., transport times, patient location information, estimated time of arrival information, etc.), physiological data or measured data, and/or alerts/alarms on the server/central computer 30. The server/central computer 30 can be located inside or outside the patient care facility environment. For example, the server/central computer 30 can be located at a nurse's station, a workstation, or other similar location within the patient care facility.

FIG. 4 illustrates a method for displaying transport indicators related to a patient on a physiological monitoring device according to one or more embodiments of the present disclosure. It is contemplated by the present disclosure that the method is implemented using the physiological monitoring device 7 described in FIGS. 1 and 2. As shown in FIG.

4, in step S40, the display/GUI 4 of the physiological monitoring device 7 displays information as a header 50 (such as that shown in FIG. 5) or other GUI that can be viewed by the patient 1 and caregiver. It is assumed that in step S40, the physiological monitoring device 7 is connected or docked to the monitor mount 10 via the connection 18 and that the monitor mount 10 is in proximity to the patient 1. The information displayed as the header is discussed in more detail with reference to FIG. 5.

Figure 5:
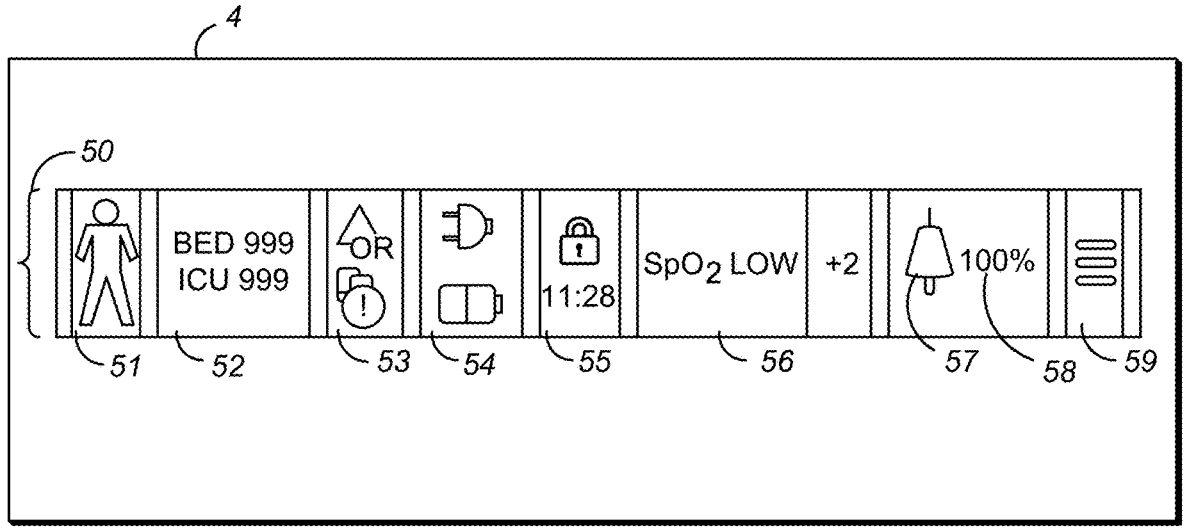
FIG. 5 illustrates an exemplary screenshot of patient information provided on a physiological monitoring device according to one or more embodiments of the present disclosure.

As shown in FIG. 5, the header 50 includes information related to a patient type 51, a bed label and care area 52, a connectivity and/or alarm indicator 53, a power source indicator 54, a digital clock and touchscreen/display locked indicator 55, an abnormal condition or alarm information indicator 56, alarm status indicator 57, and alarm volume indicator 58, and a menu icon 59.

The patient type 51 can include, for example, adult male, adult female, male child, female child, or other similar patient type information. The patient's age, weight, and/or other identifier (not illustrated) may also be displayed over the icon.

Figure 6:
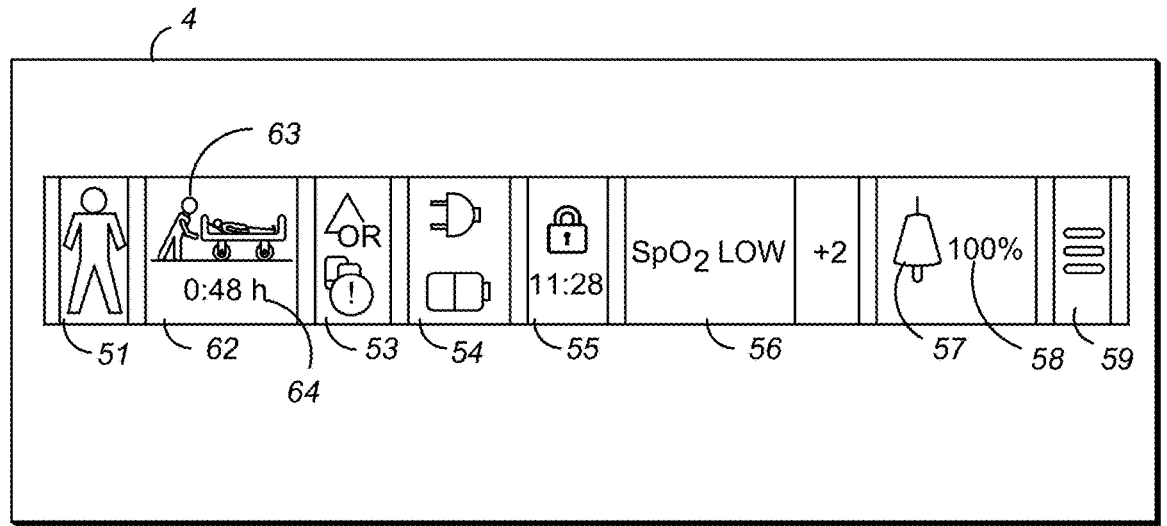
FIG. 6 illustrates an exemplary screenshot of transport indicators on a physiological monitoring device according to one or more embodiments of the present disclosure.

The bed label and care area 52 provides a bed identifier such as a bed number (e.g., Bed 999) and a location identifier of the bed within a patient care area (e.g., ICU 999 or room number) as location context information for the patient 1. As shown in FIG. 5, the physiological monitoring device 7 is connected or docked to the monitor mount 10 in the ICU 999 and in bed 999. The bed label and care area 52 may include different types of location context indicators (e.g., shown as 52 in FIGS. 5 and 62 in FIG. 6) that change and automatically update based on a patient's location and transport information. For example, when the patient is located in a patient ward or other patient care area, the bed label and care area 52 may include a bed identifier or location identifier as illustrated in FIG. 5. While the patient is in transport, the bed label and care area 52 may include a location context indicator 62 as a transport context indicator, as illustrated in FIG. 6.

The connectivity and/or alarm indicator 53 provides information regarding the connectivity status and whether one or more alarms are activated. The connectivity and/or alarm indicator 53 may be further separated into two indicators: a connectivity indicator and an alarm indicator. It is contemplated by the disclosure of the present application that the connectivity status is always indicated. On the other hand, the indication of an alarm is only shown if an alarm is activated. Otherwise, the alarm indicator is deactivated and not displayed.

The power source indicator 54 indicates the source of power (AC or battery) provided to the physiological monitoring device 7 and the level of battery charge or power source 9.

The digital clock and touchscreen/display locked indicator 55 indicates the current time and the status of the touchscreen/display lock function. When the touchscreen/display lock function is enabled, a passcode may be required to manipulate and access patient data accessible but otherwise not displayed on the display while in locked mode. In other words, while the physiological monitoring device 7 is in locked mode, only information displayed in the header 50 may be viewable to a user. The digital clock and touchscreen/display locked indicator 55 may be further separated into two indicators: a digital clock indicator and a touchscreen/display locked indicator.

The abnormal condition or alarm information indicator 56 indicates a detected abnormal physiological condition that requires the activation of a particular alarm. For example, the physiological monitoring device 7 monitors for abnormal conditions based on sensor data received from the one or more sensors 17 connected to the patient 1. In response to detecting an abnormal condition, the physiological monitoring device 7 automatically generates corresponding alarm information and displays the corresponding alarm information in the abnormal condition or alarm information indicator 56. As shown in FIG. 5, the abnormal condition detected by the physiological monitoring device 7 requiring or activating an alarm is that SpO2 is low.

The alarm status indicator 57 and alarm volume indicator 58 indicate respectively the activation of an alarm and the percentage of volume of the alarm. The alarm status indicator 57 may provide additional visual stimulus, such as blinking or flashing to attract attention to the alarm. Via the one or more processors 3 (e.g., the microcontroller 3b), the physiological monitoring device 7 may be further configured to transmit an alarm signal over the patient care facility network to another device to alert personnel to the abnormal condition.

In addition, in response to detecting an abnormal condition and identifying its type, the one or more processors 3 (e.g., the microcontroller 3b) may be configured to automatically record a start time at which the abnormal condition was initially detected and a stop time at which the abnormal condition ceased being detected, and determine an elapsed time (e.g., via a counter) that indicates a total duration over which the abnormal condition occurred. The one or more processors 3 (e.g., the microcontroller 3b) may be configured to automatically create a log entry for a patient transport log corresponding to the detected abnormal physiological event, and store the log entry in the patient transport log. The log entry may include any one of the abnormal physiological condition context information, including abnormal condition type (e.g., SpO2 low), a start time, a stop time, an elapsed time, and one or more measured physiological values corresponding to the abnormal condition.

Figure 7A:
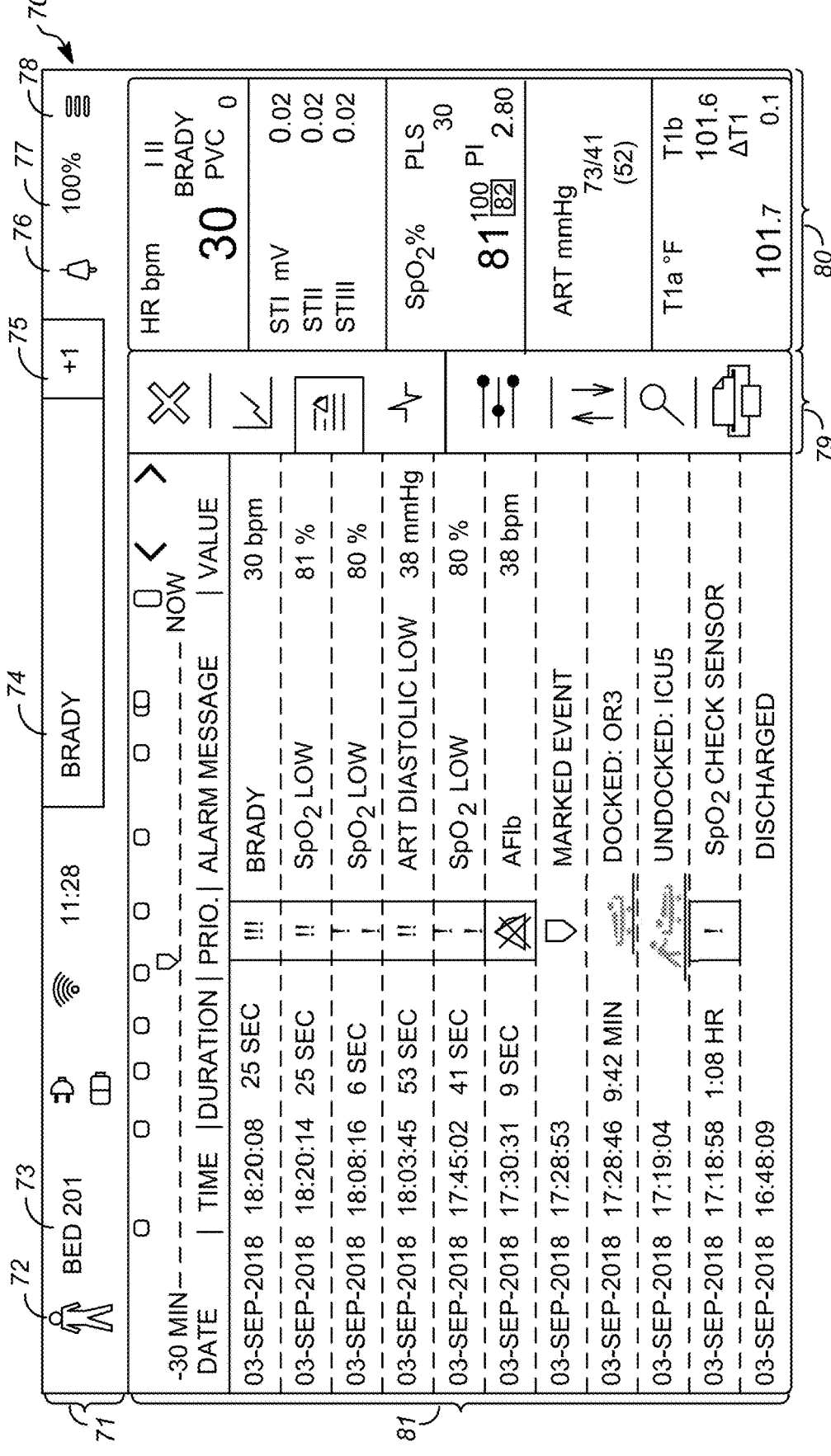
FIG. 7A illustrates an exemplary screenshot of a patient log according to one or more embodiments of the present disclosure.

The one or more processors 3 may store the patient transport log information in memory 8 and/or transmit the patient transport log information to a server (e.g., server/central computer 30) connected to the patient care communication network. For example, the server may store the patient transport log information in the patient file, such as an electronic medical record (EMR). FIG. 7A shows in more detail an exemplary patient log that may incorporate the patient transport log.

The menu icon 59 allows access to a main menu and may only be accessible when the lock function is disabled.

Returning to FIG. 4, in step S41, the undocking of the physiological monitoring device 7 is detected. The physiological monitoring device 7 is connected to the monitor mount 10 via a connection 18 that establishes a communication connection between, for example, the respective communications interfaces 6, 14 of the devices 7, 10. The connection 18 enables the monitor mount 10 to detachably secure the physiological monitoring device 7 to the monitor mount 10. In step S41, the microcontroller 3b receives an indication that the physiological monitoring device 7 is disconnected from the monitor mount 10 by, for example, a clinician or caregiver. It is contemplated by the disclosure of the present application that the physiological monitoring device 7, once disconnected or undocked from the monitor mount 10, is attached to or placed on the patient's bed so as to be transported with the patient 1. Thus, the physiological monitoring device 7 remains proximate to the patient 1 and is indicative of the patient's location.

In step S42, the display/GUI 4 changes the information displayed at the location context indicator 52, 62 to a transport indicator with timer element as the location context information for the patient 1.

FIG. 6 shows in more detail the location context information displayed on the display/GUI 4 once the physiological monitoring device 7 is disconnected or undocked from the monitor mount 10. As shown in FIG. 6, the location context portion (e.g., the bed label and care area 52) of information header 50 of FIG. 5 is replaced with a location context indicator 62 (e.g., a transport context indicator). The transport context indicator includes a patient transport icon 63 indicating that the patient 1 is in transport and a timer element 64 indicating a current duration or time lapse of the transport in progress.

Although the patient transport icon 63 is shown as a patient being pushed in a bed, this is considered merely an exemplary representation. It is contemplated by the disclosure of the present application that the patient transport icon 63 can be virtually any type of representation that conveys the movement of the patient 1.

In step S43, an undocking event, the care area, and the current date and time are stored in the patient log. In particular, the one or more processors 3 (e.g., microcontroller 3b) detects an undocking of the physiological monitoring device 7 from the monitor mount 10 initiated in step S41. In response to detecting this undocking event, the one or more processors 3 may automatically record the location information (i.e., the patient care area) in which the undocking event took place, as well as the date and time of the undocking event, as patient transport log information. The one or more processors 3 may automatically store the patient transport log information in memory 8 and/or transmit the patient transport log information to a server (e.g., server/central computer 30) connected to the patient care communication network. For example, the server may store the patient transport log information in the patient file, such as an electronic medical record (EMR). FIG. 7A shows in more detail an exemplary patient log that may incorporate the patient transport log.

In step S44, the timer element is started by the one or more processors 3 (e.g., microcontroller 3b) in response to detecting this undocking event initiated in step S41. For example, the timer element can be a stopwatch that is started once the physiological monitoring device 7 is disconnected or undocked from a first monitor mount 10 and stopped once the physiological monitoring device 7 connected or docket to a second monitor mount 10, which can be the same or a different monitor mount 10 as the first monitor mount.

As shown in FIGS. 5 and 6, the patient 1 is being moved in bed 999 from ICU 999, and 48 minutes has elapsed since the physiological monitoring device 7 was disconnected or undocked from the monitor mount 10.

In step 45, a docking event is detected by the one or more processors 3 (e.g., microcontroller 3b) that includes the connecting or docking of the physiological monitoring device 7 to a monitor mount 10 following an undocking event. The physiological monitoring device 7 is connected or docked to a monitor mount (e.g., monitor mount 10) via a connection (e.g., connection 18) that establishes a communication connection between, for example, the respective communications interfaces (e.g., communications interfaces 6, 14) of the devices (e.g., devices 7, 10) at the destination patient care area.

It is contemplated by the disclosure of the present application that the destination patient care area can be a different patient care area or the same patient care area. For example, a situation could arise that requires the patient 1 to return, for example, to ICU 999 during transport. The microcontroller 3b receives an indication that the physiological monitoring device 7 is connected to a monitor mount via the connection to the communication interface 6.

In step S46, once a docking event of the physiological monitoring device 7 is detected, the one or more processors 3 (e.g., microcontroller 3b) stops the timer element 64 and the total transport time is calculated and/or recorded by the microcontroller 3b. The total transport time is calculated based on the time that elapsed from when the physiological monitoring device 7 is initially disconnected or undocked from the monitor mount 10 in the patient care area (e.g., ICU 999) to the time that the physiological monitoring device 7 is connected or docked to a monitor mount in a destination patent care area or reconnected to the monitor mount 10 in the same patient care area (e.g., ICU 999).

In step S47, the display/GUI 4 changes the location context portion of the information header 50 (i.e., location context indicator 52, 62) from the transport context indicator (i.e., the location context indicator 62) of FIG. 6 back to the location context indicator 52 shown in FIG. 5. However, the information after being connected or docked will include location context information for the new patient care area, if applicable. Thus, the bed identifier and the patient care area identifier are updated, is applicable. The microcontroller 3b may automatically update the patient care area identifier based on location data received from the location data system 26, based on location data received from the monitor mount 10 stored in memory 13, based on a patient care schedule accessed from memory 8, memory 13, or the server/central computer 30, or may be manually updated based on user input.

In step S48, a docked event, the care area, the current date and time, and the total transport time are stored in, for example, a patient transport log. For example, in response to detecting this docking event, the one or more processors 3 may record the location information (i.e., the care area) in which the docking event took place, as well as the date and time of the docking event and the total transport time, as patient transport log information. The one or more processors 3 may store the patient transport log information in memory 8 and/or transmit the patient transport log information to a server (e.g., server/central computer 30) connected to the patient care communication network. For example, the server may store the patient transport log information in the patient file, such as an EMR. FIG. 7A shows in more detail an exemplary patient log that may incorporate the patient transport log.

The use of transport time indicators as described with reference to FIGS. 4-6 allows clinicians to have a quick reference to the duration of a patient transport to help manage medicines, and patient comfort and care. Additionally, transport location information can support patient care facility emergency code situations in which a crisis team is required to intervene by communicating the patient's location and offering an estimated time to arrival for assistance.

FIG. 7A illustrates an exemplary screenshot of a patient log screen according to one or more embodiments of the present disclosure. As shown in FIG. 7A, a patient log screen 70 includes a header 71, an event log 81, a display selector 79, and physiological parameter values 80. The fields of the patient log screen 70 in FIG. 7A are meant to be exemplary fields provided in a patient log screen 70 and are in no way meant to limit the number or types of fields that can be included in the patient log screen 70. For example, it is contemplated by the disclosure of the present application that many different alarm status fields can be added to the patient log screen 70 without departing from the spirt and scope of the present disclosure. As noted above, the patient log screen may incorporate one or more aspects of the patient transport log.

As shown in FIG. 7A, the header 71 includes similar information to the header 50 shown in FIG. 4. For example, the header 71 includes a patient type 72, a bed label 73, alarm indicator 74, additional alarms 75, alarm status indicator 76, alarm volume indicator 77, and a menu icon 78.

The event log 81 includes information regarding the care of a particular patient (e.g., the existence of a Brady heart rate alarm) from the start of patient care within a patient care facility environment to the patient's discharge. For example, the event log 81 of the patient log screen 70 incudes information that concisely documents the movements of the patient between patient care areas, duration of movement or care, priority levels, alarms, and physiological data measured on a particular day (e.g., Sep. 3, 2018 between 16:48:09-18:20:08).

As shown in FIG. 7A, the event log 81 also includes at least two rows related to the transport of the patient, which depicts an undocked state (e.g., an icon of a person pushing a patient in a bed) and a docked state (e.g., an icon of a patient in a bed). It is contemplated by the disclosure of the present application that the icons representing the undocked state and docked state in the event log 81 are exemplary icons and are in no way meant to limit the icons that can be used to represent the undocked state and docked state in the event log 81. In this example, events are listed chronologically from most recent at the top to least recent at the bottom.

In this example, it is shown that the "UNDOCKED: ICU5" event under "ALARM MESSAGE" is followed by the "DOCKED: OR3", indicating that the microcontroller 3b detected the undocking event, recorded the time of the undocking event and started a transport timer, and subsequently detected a docking event, recorded the time of the docking event, and recorded the elapsed total transport time under "DURATION" between the undocking event and the docking event. Here, the patient was in transport for 9:42 minutes. Patient care area identifiers "ICU5" and "OR3" are also recorded by the microcontroller 3b to indicate the location of the undocking and docking events.

Additionally, although the event log 81 in FIG. 7A shows the "UNDOCKED: ICU5" event immediately followed by the "DOCKED: OR3" event, it is contemplated by the disclosure of the present application that the event log 81 could include additional information regarding events that occurred between the "UNDOCKED: ICU5" event and the "DOCKED: OR3" event, as shown in FIG. 7B.

FIG. 7B illustrates a segment of a patient transport log of event log 81 according to one or more embodiments of the present disclosure. The segment includes additional events detected by the physiological monitoring device 7 between undocking and docking events, where the "TIME" is a timestamp of a time an event is initially detected, "DURATION" is an elapsed time the event occurred, "PRIO." indicates the priority of a triggered alarm based on the critical nature of the detected abnormal physiological event to the patient's health, "ALARM MESSAGE" indicates the type of event (e.g., the type of abnormal physiological event), and "VALUE" indicates a measured physiological value corresponding to the event.

As shown in FIG. 7B, the following alarms occurred during transport of the patient: SpO2 check sensor, RR interval (RRi) high, arterial invasive pressure (ART) out of range low, and heart rate (HR) low. Similar events could also be detected while the physiological monitoring device 7 is docked (i.e., not in transport).

The information in the patient transport log shown in FIG. 7B helps a clinician to understand the events that occurred during the transport of the patient (e.g., between the undocked and docked events). Additionally, such transparency (e.g., with regard to the patient's condition) can help a clinician to make better clinical decisions.

The display selector 79 allows a user to transition between different screens or GUIs for obtaining different information related to the patient. The physiological parameter values 80 include real-time physiological data measured by sensors 17 connected to the patient. The patient log screen 70 shown in FIGS. 7A and 7B can be used by clinicians, caregivers, and patient care facility management to maintain patient care facility analytics, assess overall patient care, and help to determine areas for improvement in patient care.

Figure 8:
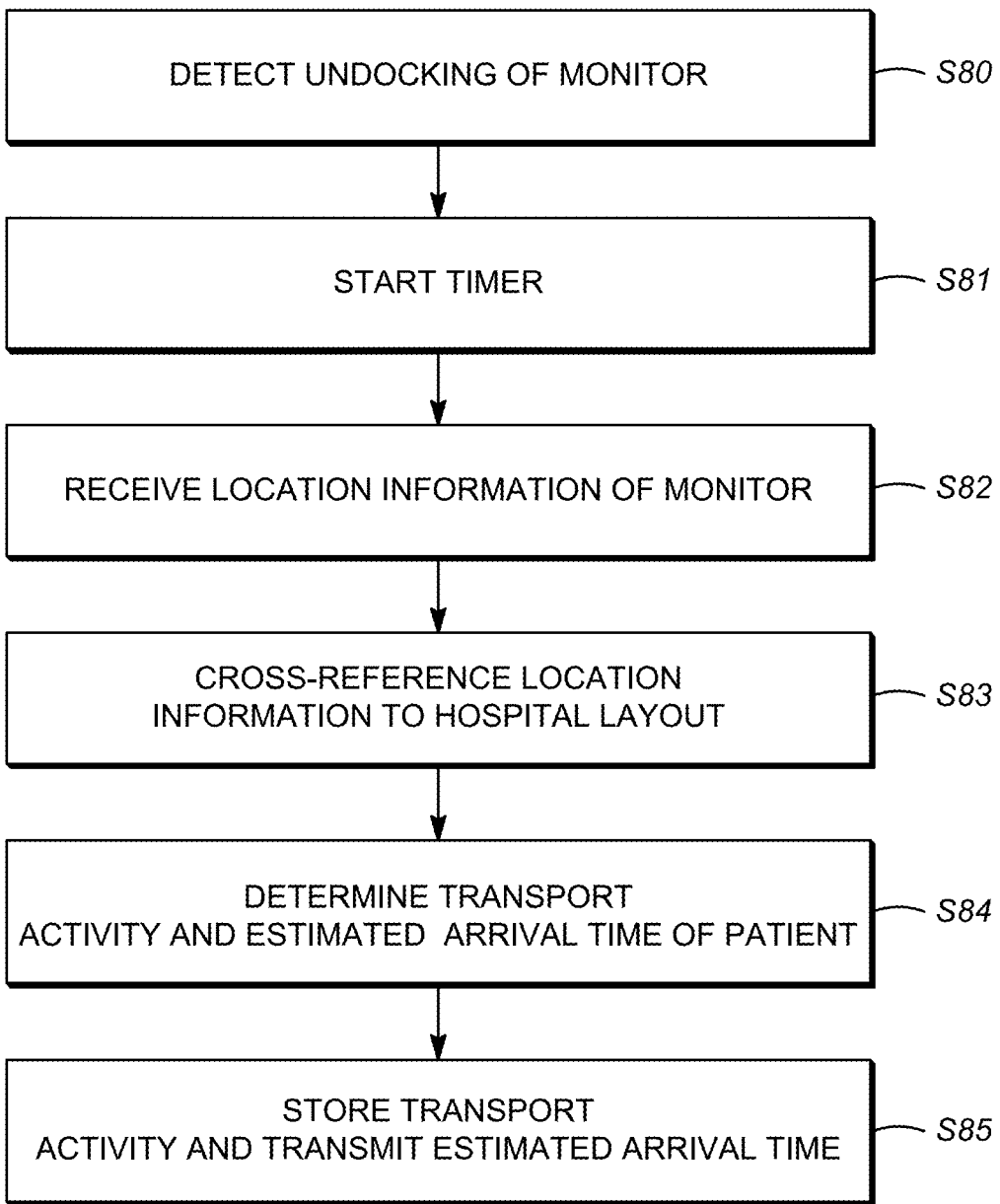
FIG. 8 illustrates a method for determining an estimated time of arrival of a patient according to one or more embodiments of the present disclosure.

FIG. 8 illustrates a method for determining an estimated time of arrival of a patient according to one or more embodiments of the present disclosure. In step S80, the physiological monitoring device 7 detects that is has been disconnected or undocked from the monitor mount 10.

In step S80, the microcontroller 3b detects or receives an indication that the physiological monitoring device 7 is disconnected from the monitor mount 10. Once disconnected or undocked from the monitor mount 10, the physiological monitoring device 7 is attached to or placed on the patient's bed so as to be transported with the patient 1.

In step S81, the timer element is started by, for example, the microcontroller 3b. In particular, the timer element (e.g., timer element 64) is started in response to the physiological monitoring device 7 being disconnected or undocked from the monitor mount 10.

In step S82, location information of the physiological monitoring device 7 is received by the microcontroller 3b from the location data system 26. As discussed with reference to FIG. 2, the physiological monitoring device 7 includes the location data system 26 that can be connected to the communication interface circuitry of microcontroller 3b so that the physiological monitoring device 7 can transmit the location of the patient at all times including the location of the patient during transport to the clinician, caregiver, or other devices. Additionally, the location of the patient can be used by the microcontroller 3b to determine an estimated time of arrival of the patient.

In step S82, the microcontroller 3b receives location data provided by the location data system 26.

In step S83, the microcontroller 3b determines a final transport destination (i.e., an expected patient care area) based on a patient care schedule (e.g., treatment or procedure scheduled for the patient in a patient care area within the patient care facility) or based on manual input from a user. The patient care schedule may include schedule of patient care areas to which the patient is to be transported from and to. The patient care areas most proximate in time to the current time may be selected by the microcontroller 3b as the final transport destination.

The microcontroller 3b further compares the received (current) location data provided by the location data system 26 with the final transport destination, cross-references the received (current) location and the final transport destination to a patient care facility layout or a patient care facility map along with information related to a patient care schedule (e.g., treatment or procedure scheduled for the patient in a patient care area within the patient care facility) to determine a remaining route of transport patient care schedule

Based on the cross-referenced results, in step S83, the microcontroller 3b determines the estimated time of arrival (ETA) of the patient to an expected patient care area within the patient care facility in step S84. In step S85, the ETA can be transmitted by the communication interface circuitry of microcontroller 3b to, for example, the patient care facility wireless communications system and stored in the patient log.

Transport location information and ETA can support patient care facility emergency code situations in which a crisis team is required to intervene by communicating the patient's location and ETA. It is contemplated by the disclosure of the present application that an accelerometer, a GPS, and/or other location technology may provide intelligence about when a patient transport is actually occurring and can be used to refine the detection of a transport activity. The GPS or location technology can be used along with a patient care facility layout or a patient care facility map to track the location of a patient in an event of a patient care facility emergency code, which could be used to communicate information to a crises team (e.g., where to locate the patient and the ETA of the patient to a patient care area, such as an operating room).

It is also contemplated by the disclosure of the present application that an accelerometer, GPS, or other location technology can be used along with a patient care facility layout or a patient care facility map and patient care facility scheduling system to determine an ETA to another patient care area, and provide underlying data to support the optimization of transport paths and care area scheduling. Additionally, the accelerometer, GPS, or other location technology can be used along with a patient care facility layout or a patient care facility map to enable workflow analytics to be captured, retrieved, an analyzed for improving patient transport efficiencies.

Figure 9:
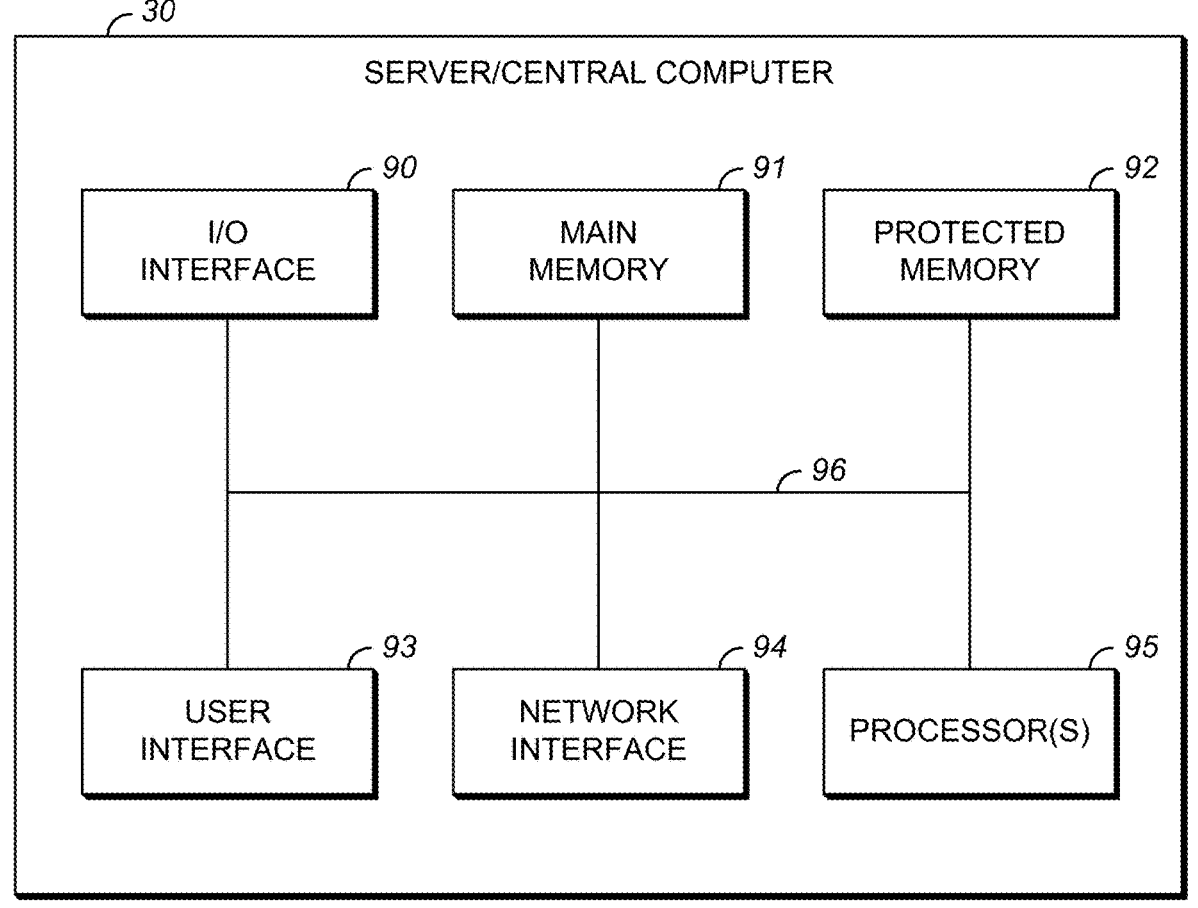
FIG. 9 is a schematic diagram of an exemplary server or central computer according to one or more embodiments of the present disclosure.

FIG. 9 is a schematic diagram of an exemplary server or central computer according to one or more embodiments of the present disclosure. It is contemplated by the present disclosure that the server/central computer 30 may be implemented in the patient care facility environment, or implemented separate from the patient care facility environment. It is also contemplated by the present disclosure that the server/central computer 30 includes electronic components or electronic computing devices operable to receive, transmit, process, store, and/or manage patient data and information associated with the transport and status of patients, which encompasses any suitable processing device adapted to perform computing tasks consistent with the execution of computer-readable instructions stored in memory or computer-readable recording medium.

As shown in FIG. 9, the exemplary server/central computer 30 includes a main memory 91, a protected memory 92, an I/O interface 90, a user interface 93, a network interface 94, and one or more processors 95. The main memory 91 can be a single memory device or a multi-memory device, including RAM, a memory buffer, a hard drive, a database, an EPROM, an EEPROM, a ROM, a flash memory, hard disk, or various layers of memory hierarchy. The main memory 91 can be used to store any type of instructions associated with algorithms, processes, or operations for controlling the general functions of the server/central computer 30 as well as any operating system such as Linux, UNIX, Windows Server, or other customized and proprietary operating systems.

The protected memory 92 is, for example, a processor reserved memory of dynamic random access memory (DRAM) or other reserved memory module or secure memory location for storing more critical information such as confidential or proprietary patient information.

The I/O interface 90 can be an iinterface for enabling the transfer of information between server/central computer 30, one or more physiological monitoring devices 7, and external devices such as peripherals connected to the server/central computer 30 that need special communication links for interfacing with the one or more processors 95. The I/O interface 90 can be implemented to accommodate various connections to the server/central computer 30 that include, but is not limited to, a USB connection, parallel connection, a serial connection, coaxial connection, an HDMI connection, or any other electrical connection used for connecting to and interfacing with external devices.

The user interface 93 is implemented for allowing communication and interaction between a user and the server/central computer 30. The user interface 93 includes, but is not limited to, a mouse, a keyboard, an LCD display, a CRT display, a TFT display, an LED display, an HD display, or other similar display device that may include touch screen capabilities.

The network interface 94 is a software and/or hardware interface implemented to establish a connection between the server/central computer 30 and one or more physiological monitoring devices or other servers/central computer inside and outside the patient care or patient care facility environment.

It is contemplated by the present disclosure that that network interface 94 includes software and/or hardware interface circuitry for establishing communication connections with the rest of the system using both wired and wireless connections for establishing connections to, for example, a local area networks (LANs), wide area networks (WANs), metropolitan area networks (MANs) personal area networks (PANs), and wireless local area networks (WLANs), system area networks (SANs), cloud, and other similar networks.

The one or more processors 95 are used for controlling the general operations of the server/central computer 30. Each one of the one or more processors 95 can be, but are not limited to, a CPU, a hardware microprocessor, a multi-core processor, a single core processor, an FPGA, a microcontroller, an ASIC, a DSP, or other similar processing device capable of executing any type of instructions, algorithms, or software for controlling the operation of the server/central computer 30.

Communication between the components of the server/central computer 30 (e.g., 90-94) are established using an internal bus 96.

The present disclosure may be implemented as any combination of an apparatus, a system, an integrated circuit, and a computer program on a non-transitory computer readable recording medium. The one more processors may be implemented as an integrated circuit (IC), an application specific integrated circuit (ASIC), or large scale integrated circuit (LSI), system LSI, super LSI, or ultra LSI components which perform a part or all of the functions described in the present disclosure.

The present disclosure includes the use of computer programs or algorithms. The programs or algorithms can be stored on a non-transitory computer-readable medium for causing a computer, such as the one or more processors, to execute the steps described in FIGS. 4-8. For example, the one or more memories stores software or algorithms with executable instructions and the one or more processors can execute a set of instructions of the software or algorithms in association with executing generating and displaying transport indicators and other patient information, as described with reference to FIGS. 4-8.

The computer programs, which can also be referred to as programs, software, software applications, applications, components, or code, include machine instructions for a programmable processor, and can be implemented in a high-level procedural language, an object-oriented programming language, a functional programming language, a logical programming language, or an assembly language or machine language. The term computer-readable recording medium refers to any computer program product, apparatus or device, such as a magnetic disk, optical disk, solid-state storage device, memory, and programmable logic devices (PLDs), used to provide machine instructions or data to a programmable data processor, including a computer-readable recording medium that receives machine instructions as a computer-readable signal.

By way of example, a computer-readable medium can comprise DRAM, RAM, ROM, EEPROM, CD-ROM or other optical disk storage, magnetic disk storage, or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The term "processor" or "processing circuitry" may generally refer to any of the foregoing logic circuitry, alone or in combination with other logic circuitry, or any other equivalent circuitry. A control unit including hardware may also perform one or more of the techniques of this disclosure. A control unit may use electrical signals and digital algorithms to perform its receptive, analytic, and control functions, which may further include corrective functions. Such hardware, software, and firmware may be implemented within the same device or within separate devices to support the various techniques described in this disclosure.

It is further to be noted that methods disclosed in the specification or in the claims may be implemented by a device having means for performing each of the respective acts of these methods.

Further, it is to be understood that the disclosure of multiple acts or functions disclosed in the specification or claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

Use of the phrases "capable of," "capable to," "operable to," or "configured to" in one or more embodiments are mutually exchangeable, and refers to some apparatus, logic, hardware, and/or element designed in such a way to enable use of the apparatus, logic, hardware, and/or element in a specified manner. The subject matter of the present disclosure is provided as examples of apparatus, systems, methods, and programs for performing the features described in the present disclosure. However, further features or variations are contemplated in addition to the features described above. It is contemplated that the implementation of the components and functions of the present disclosure can be done with any newly arising technology that may replace any of the above implemented technologies.

Additionally, the above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

What is claimed is:

1. A physiological monitoring device comprising:
a sensor interface configured to receive physiological data from at least one physiological sensor connected to a patient;
a display configured to display information relating to the patient including transport indicators related to a patient transport; and,
at least one processor configured to:
operate the physiological monitoring device in a non-transport mode while docked to one of at least one monitor mount;
display first location context information corresponding to a first patient care area on the display of the physiological monitoring device while the physiological monitoring device is in the non-transport mode in the first patient care area;
detect an undocking event in response to undocking the physiological monitoring device from a first monitor mount of the at least one monitor mount, wherein the first monitor mount is located in the first patient care area;
access a patient care schedule and determine a transport destination based on the patient care schedule, wherein the patient care schedule includes a plurality of patient care areas linked to a corresponding schedule time;
compare an electronic time stamp of the detected undocking event to schedule times in the patient care schedule, and select a patient care area from the plurality of patient care areas having a schedule time most proximate to the electronic time stamp of the detected undocking event as the transport destination; and,
in response to detecting the undocking event, automatically switching the physiological monitoring device to a transport mode, the transport mode including changing the first location context information to transport context information on the display.

2. The physiological monitoring device of claim 1, wherein the at least one processor is further configured to detect a docking event in response to docking the physiological monitoring device to the first monitor mount; and operate the physiological monitoring device into the non-transport mode in response to detecting the docking event, including displaying the first location context information on the display.

3. The physiological monitoring device of claim 2, wherein the first location context information includes a patient bed identifier and a first patient care area identifier corresponding to a location of the patient.

4. The physiological monitoring device of claim 1, wherein the at least one processor is further configured to:
in response to detecting the undocking event, start a timer and display the timer as the transport context information.

5. The physiological monitoring device of claim 4, wherein the at least one processor is further configured to:
while operating in the transport mode resulting from the undocking event, detect a docking event in response to docking the physiological monitoring device to the first monitor mount or to a second monitor mount; and
in response to detecting the docking event, operate the physiological monitoring device in the non-transport mode, including stopping the timer and storing a total transport time that elapsed from the undocking event to the docking event in a patient log.

6. The method of claim 1, wherein the at least one processor is further configured to:
while operating in the transport mode resulting from the undocking event, detect a docking event in response to docking the physiological monitoring device to the first monitor mount or to a second monitor mount; and
in response to detecting the docking event, operating the physiological monitoring device in the non-transport mode, including changing the transport context information on the display to the first location context information corresponding to the first patient care area of the first monitor mount or to second location context information corresponding to a second patient care area of the second monitor mount.

7. The physiological monitoring device of claim 1, further comprising:
a location detector configured to detect a location of the physiological monitoring device; wherein the at least one processor is further configured to:
in response to detecting the undocking event, access the patient care schedule of the patient and determine the transport destination of the patient based on the patient care schedule;
receive a detected location of the physiological monitoring device from the location detector while the physiological monitoring device is operating in the transport mode; and
calculate an estimated time of arrival to the transport destination based on the detected location.

8. The physiological monitoring device of claim 1, wherein the at least one processor is configured to calculate the estimated time of arrival to the transport destination based on cross-referencing the detected location and the transport destination to a patient care facility layout.

9. The physiological monitoring device of claim 8, further comprising a transmitter configured to transmit the detected location to an external device that is connected to the physiological monitoring device via a communication network.

10. The physiological monitoring device of claim 9, wherein:
the location detector is configured to detect an updated location of the physiological monitoring device at regular intervals while the physiological monitoring device is operating in the transport mode; and the at least one processor is configured to update the estimated time of arrival based on the updated location.

11. The physiological monitoring device of claim 10, further comprising:
a transmitter configured to transmit the estimated time of arrival to an external device that is connected to the physiological monitoring device via a communication network.

12. The physiological monitoring device of claim 1, further comprising: wherein the transport context information comprises an icon signifying that a patient transport is in progress and a timer displaying the elapsed time of the patient transport.

13. The physiological monitoring device of claim 1, wherein the location detector includes GPS technology.

14. A physiological monitoring device, comprising:
a sensor interface configured to receive physiological data from at least one physiological sensor connected to a patient;
a display configured to display information related to the patient; and
at least one processor configured to:
operate the physiological monitoring device into a non-transport mode while docked to one of at least one monitor mount;
display first location context information corresponding to a first patient care area on the display while the physiological monitoring device is operating in the non-transport mode in the first patient care area;
detect an undocking event in response to undocking the physiological monitoring device from a first monitor mount of the at least one monitor mount, wherein the first monitor mount is located in the first patient care area; and
in response to detecting the undocking event, operate the physiological monitoring device in a transport mode, including changing the first location context information to transport context information on the display, wherein the transport context information comprises an icon signifying that a patient transport is in progress and a timer displaying the elapsed time of the patient transport.

15. A physiological monitoring device, comprising:
a sensor interface configured to receive physiological data from at least one physiological sensor connected to a patient;
a display configured to display information related to the patient; and
at least one processor configured to:
operate the physiological monitoring device into a non-transport mode while docked to one of the at least one monitor mount;
detect an undocking event in response to undocking the physiological monitoring device from a first monitor mount of the at least one monitor mount, wherein the first monitor mount is located in the first patient care area;
in response to detecting the undocking event, automatically switch the physiological monitoring device to a transport mode, including changing the first location context information to transport context information on the display, wherein the transport context information comprises an icon signifying that a patient transport is in progress and a timer displaying the elapsed time of the patient transport; and
while in transport mode, correlating location data with information related to a patient care schedule.

16. The physiological monitoring device of claim 15, further configured to:
determine a next scheduled patient event from the patient care schedule, the next scheduled patient event being at least one selected from the group of: a next scheduled administration of medicine and a next scheduled administration of treatment; and
active an alarm if a time for the next scheduled patient event has passed and the physiological monitoring device is in a transport mode.

17. The physiological monitoring device of claim 15, wherein:
the location detector is configured to detect an updated location of the physiological monitoring device at regular intervals while the physiological monitoring device is operating in the transport mode; and
the at least one processor is configured to update the estimated time of arrival based on the updated location.

* * * * *